United States Patent
Bostick et al.

(10) Patent No.: US 9,717,607 B1
(45) Date of Patent: Aug. 1, 2017

(54) AUGMENTED CONTROL OF ROBOTIC PROSTHESIS BY A COGNITIVE SYSTEM

(71) Applicant: International Business Machines Corporation, Armonk, NY (US)

(72) Inventors: James E. Bostick, Cedar Park, TX (US); John M. Ganci, Jr., Cary, NC (US); Martin G. Keen, Cary, NC (US); Sarbajit K. Rakshit, Kolkata (IN); Craig M. Trim, Sylmar, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/337,207

(22) Filed: Oct. 28, 2016

(51) Int. Cl.
| | |
|---|---|
| *B25J 9/16* | (2006.01) |
| *A61F 2/70* | (2006.01) |
| *G05B 19/048* | (2006.01) |
| *A61F 2/68* | (2006.01) |

(52) U.S. Cl.
CPC .......... *A61F 2/70* (2013.01); *A61F 2/68* (2013.01); *B25J 9/161* (2013.01); *G05B 19/048* (2013.01); *A61F 2002/6827* (2013.01); *A61F 2002/701* (2013.01); *A61F 2002/704* (2013.01); *G05B 2219/45172* (2013.01)

(58) Field of Classification Search
CPC ........ A61F 2/54; A61F 2002/704; A61F 2/72; A61F 2/68; G06T 7/20; B25J 9/161; B25J 13/08; B25J 9/1697; Y10S 707/99932; Y10S 901/27
USPC ..... 700/246, 259; 706/45, 50; 382/103, 107, 382/156; 623/24, 25
See application file for complete search history.

(56) References Cited

U.S. PATENT DOCUMENTS

| | | | |
|---|---|---|---|
| 5,299,288 A | 3/1994 | Glassman et al. | |
| 5,845,048 A | 12/1998 | Masumoto | |
| 7,826,894 B2 | 11/2010 | Musallam et al. | |
| 9,002,098 B1 * | 4/2015 | Chelian | G06T 7/74 382/153 |
| 2003/0031357 A1 | 2/2003 | Wenzel et al. | |

(Continued)

OTHER PUBLICATIONS

Cao, Jerry, "How to design websites that mirrow how our eyes work", printed Aug. 28, 2015, 4 pages.

(Continued)

*Primary Examiner* — Dalena Tran
(74) *Attorney, Agent, or Firm* — Daniel R. Simek

(57) ABSTRACT

Embodiments of the present invention provides for one or more processors receive image data of an object selected by a user and determine image attributes of the object selected, based on image analytics on the image data. One or more processors determine whether the image attributes of the object selected match an identified object of a knowledge base, in which an identified object includes image attributes and manipulation data corresponding to the identified object, and responsive to determining that the object selected by the user of the prosthetic device matches an identified object of the knowledge base, one or more processors transmits manipulation data corresponding to the identified object matching the object selected by the user, to a mobile controlling device communicatively connected to the prosthetic device, wherein the mobile controlling device applies the manipulation data corresponding to the identified object to the prosthetic device.

24 Claims, 4 Drawing Sheets

(56) References Cited

U.S. PATENT DOCUMENTS

| | | | |
|---|---|---|---|
| 2013/0343640 A1* | 12/2013 | Buehler | B25J 9/0087 |
| | | | 382/155 |
| 2014/0336781 A1 | 11/2014 | Katyal et al. | |
| 2014/0371871 A1 | 12/2014 | Farina et al. | |
| 2015/0005622 A1 | 1/2015 | Zhao et al. | |
| 2015/0199824 A1 | 7/2015 | Kim et al. | |

OTHER PUBLICATIONS

Ali, et al., "Analysis of Finger Movement for Robotic Hand (MAPRoh-1) by Using Motion Capture and Flexible Bend Sensor", Chapter 3, The 8th International Conference on Robotic, Vision, Signal Processing & Power Applications, Lecture Notes in Electrical Engineering 291, © Spring Science + Business Media Singapore 2014, printed Nov. 23, 2015, pp. 23-29.

Lavars, Nick, "Vibrating glove teaches Braille through passive haptic learning", gixmag.com/wearable-glove-read-write-braille/32729/, printed Aug. 28, 2015, 3 pages.

* cited by examiner

AUGMENTED CONTROL OF ROBOTIC PROSTHESIS BY A COGNITIVE SYSTEM

FIELD OF THE INVENTION

The present invention relates generally to the field of prosthetic control, and more particularly to applied probability to prosthetic control by a cognitive system.

BACKGROUND OF THE INVENTION

A prosthetic device, also referred to as a prosthesis, is used to replace a missing body part, or augment a non-functioning body part. Various prosthetic devices have been in use for a long time, and through advancement of technology applied to prosthesis, people that have lost the use of limbs through trauma or disease, or those who from birth lack function of a body appendage, have been able to regain some level of function from technologically assisted prosthetics.

Some modern prosthetics make use of electro-mechanical functioning, and in some cases bio-mechanical control, to assist the user in performing basic function. The technologically assisted prosthetics often lack the fine motor control, accuracy, and speed of interaction that their biological counterparts achieve by repetitive use and learning.

SUMMARY

Embodiments of the present invention disclose a method, computer program product, and system that provides for one or more processors to receive image data of an object selected by a user. One or more processors determine image attributes of the object selected, based on performing image analytics on the image data. One or more processors determine whether the image attributes of the object selected match an identified object of a knowledge base that includes a plurality of identified objects, in which an identified object of the plurality of identified objects of the knowledge base includes image attributes and manipulation data corresponding to the identified object, and responsive to determining that the object selected by the user of the prosthetic device matches an identified object of the knowledge base, one or more processors transmits manipulation data corresponding to the identified object matching the object selected by the user, to a mobile controlling device communicatively connected to the prosthetic device, wherein the mobile controlling device applies the manipulation data corresponding to the identified object to the prosthetic device.

DETAILED DESCRIPTION

Figure 1:
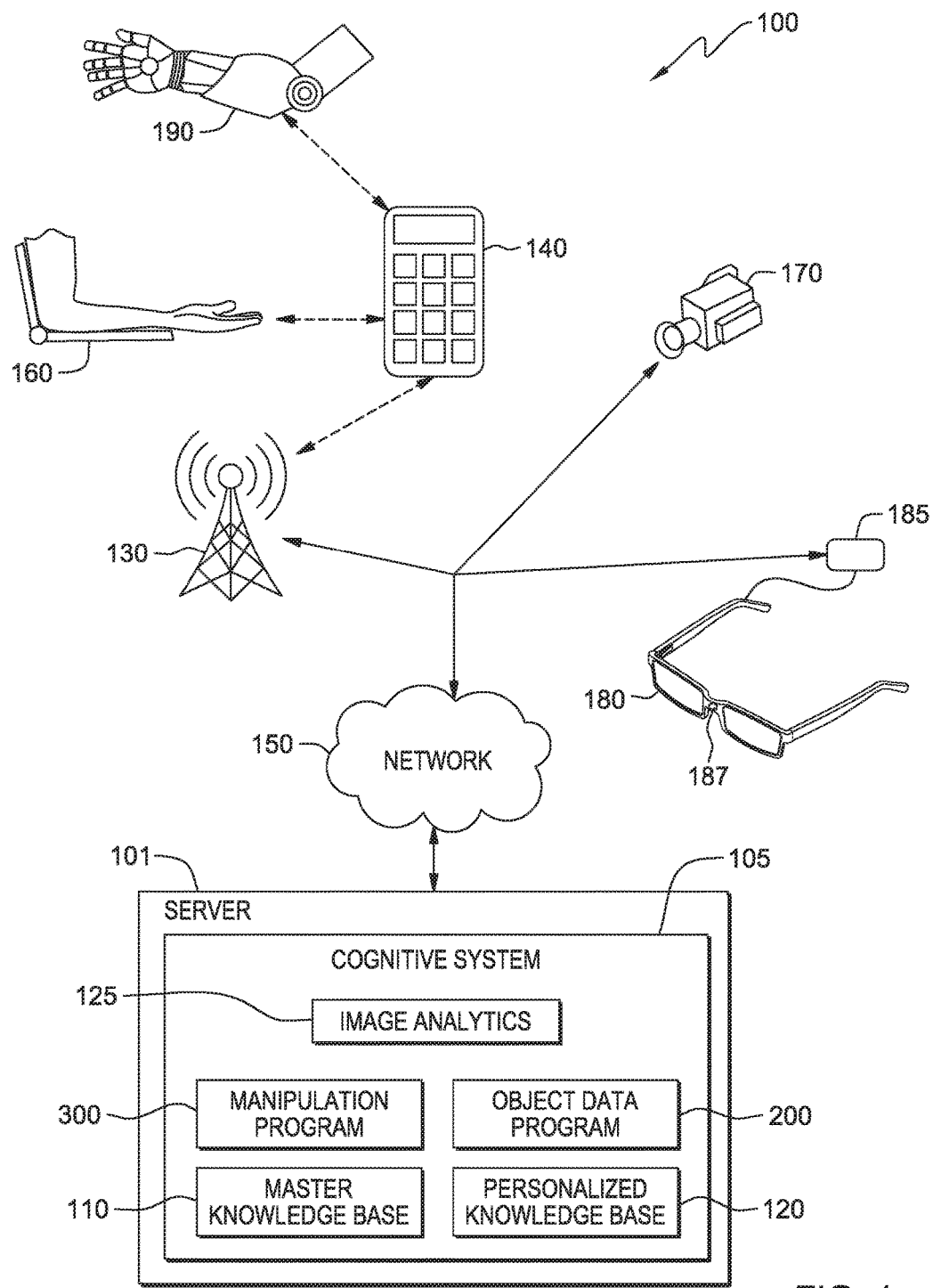
FIG. 1 is a functional block diagram illustrating a distributed data processing environment, in accordance with an embodiment of the present invention.

Embodiments of the present invention recognize that utilizing prosthetic devices to grasp and manipulate objects can require tedious adjustments and trials to obtain a functional set of parameters to successfully utilize the object. An object may require a certain amount of pressure, texture sensitivity, and lifting force to properly grasp and manipulate the object. In some cases, the set of parameters are considered attributes of a pattern of manipulation of an object, such as grasping an object, may change in order to further manipulate the object. Various objects a user grasps may each have a particular set of manipulation parameters, with the parameter sets varying widely. Users of prosthetic devices may struggle with the judgement and adjustments needed to attain the fine motor control, accuracy, and speed in utilizing the prosthetic device.

In some embodiments of the present invention, use of a robotic prosthesis device is augmented with mobile connectivity to a remote cognitive system, which provides manipulation intelligence, improving manipulation of an object, including increased fine motor control, grasping sensitivity, accuracy, and speed of manipulation of the object. The cognitive system performs image analytics to identify an object within a camera image, and includes the capability to search a knowledge base of multiple defined objects to determine a match of a particular object, based on the image analytics. Embodiments of the present invention utilize a knowledge base that includes data for the manipulation of an object corresponding to the image analytics by a prosthetic device. Eye focus, facial expression, body movement, biometrics, and local sensor haptic feedback are used to determine the object and task intended by a user of a prosthetic device. The cognitive system determines if a threshold of confidence is exceeded in matching an object image to a defined object in the knowledge base and responds to exceeding the threshold by transmitting the manipulation data corresponding to the identified object to a mobile device controlling the prosthetic device.

In some embodiments of the present invention, the manipulation data for a prosthetic device provides augmented assistance for manipulation of a recognized object and task of a user. In embodiments in which an object isn't identified within a knowledge base, or a user task is not recognized, the robotic prosthetic device is operated by another source; however, the image and manipulation data from operation by the other source is applied to machine learning techniques to augment and/or improve the object identification data and manipulation data within the knowledge base and enable subsequent augmented manipulation assistance.

Some embodiments of the present invention include a personalized knowledge base located local to the mobile controlling device of the prosthesis, which contains manipulation data for objects that are refined to the particular prosthetic device and its user. The manipulation data included in the personalized knowledge base is refined by machine learning performed on data received from multiple iterations of an object over time. In some embodiments of the present invention, manipulation data is continually received and transmitted to the cognitive system for continuous machine learning and refinement of manipulation data associated with a particular object.

Some embodiments of the present invention may be directed to a manipulation device that may not function directly as a prosthetic device, but is enabled to receive and apply transmitted manipulation data of a selected object from a repository, or knowledge base that includes a plurality of identified objects and corresponding manipulation data, previously generated for the individual identified objects of the plurality of identified objects.

The present invention will now be described in detail with reference to the Figures. FIG. 1 is a functional block diagram illustrating a distributed data processing environment, generally designated 100, in accordance with an embodiment of the present invention. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes wireless connection 130, mobile control device 140, robotic support device 160, camera 170, augmented reality (AR) glasses 180, AR glasses transceiver 185, AR glasses camera 187, robotic prosthetic device 190, and server 101, which further includes cognitive system 105. Cognitive system 105, in some embodiments, is depicted as operating remotely to mobile control device 140, and including master knowledge base 110, personalized knowledge base 120, object data program 200, and manipulation program 300. In some embodiments of the present invention, mobile control device 140 is wirelessly connected to wireless connection 130, and in some embodiments of the present invention, wirelessly connected to robotic prosthetic device 190, and in other embodiments, wirelessly connected to robotic support device 160. In some embodiments of the present invention, personalized knowledge base 120 is included in mobile control device 140. Cognitive system 105, master knowledge base 110, personalized knowledge base 120, wireless connection 130, camera 170 and AR glasses transceiver 185, are all interconnected via network 150.

Network 150 can be, for example, a local area network (LAN), a telecommunications network, a wide area network (WAN), such as the Internet, a virtual local area network (VLAN), a bus connection of an integrated device, or any combination that can include wired, wireless, or optical connections. Network 150 can include one or more wired and/or wireless networks, such as a connection to wireless connection 130, which are capable of receiving and transmitting data, text, voice, images, program instructions, and/or video signals, including multimedia signals that include text, voice, data, and video information. In general, network 150 can be any combination of connections and protocols that will support communications between cognitive system 105 hosted on server 101, AR glasses transceiver 185, wireless connection 130, mobile control device 140, and camera 170.

Wireless connection 130 provides communication between mobile control device 140 and AR glasses transceiver 185, camera 170 and, via network 150, to cognitive system 105. Wireless connection 130, properly configured, can provide wireless connectivity, for example, through BLUETOOTH®, Wi-Fi, radio, ZigBee®, or infrared technology (ZigBee is a registered trademark of ZigBee Alliance in the U.S. and other countries worldwide; BLUETOOTH is a trade mark of the Bluetooth Special Interest Group (SIG), Inc., in the U.S. and other countries worldwide). In some embodiments, wireless connection 130 may use WiMAX® technology (WiMAX is a registered trademark of WiMAX Forum in the U.S and in other countries worldwide), or include configuration to utilize 3G, 4G, or future extensions of such wireless network technologies to connect mobile control device 140 to robotic prosthetic device 190, robotic support device 160, or signal and sensor inputs from AR glasses transceiver 185, and camera 170.

Mobile control device 140 receives manipulation data from cognitive system 105, retrieved from personalized knowledge base (KB) 120, or master knowledge base (KB) 110, and performs operational motor control of a prosthetic device to which it is wirelessly connected, such as robotic prosthetic device 190. Mobile control device 140 is connected to wireless connection 130, communicating to cognitive system 105 via network 150. In some embodiments of the present invention, mobile control device 140 is positioned in the vicinity of the user of the robotic prosthetic device, such as robotic prosthetic device 190. In some embodiments, mobile control device 140 may be attached or worn by the user. Mobile control device 140 includes computing capability to process instructions directed to motors and other electronic components enabling the mobility and manipulation of the prosthetic device. In some embodiments of the present invention, mobile control device 140 is a smart phone configured with memory and processing power to receive manipulation data from cognitive system 105 and wirelessly operate the motors and electronic components enabling precise sensory input and movement of robotic prosthetic device 190. In other embodiments, mobile control device 140 is constructed specifically for receiving prosthetic control manipulation data wirelessly and transforming the data to specific instructions directed to the operational components of the prosthetic device. In some embodiments of the present invention, mobile control device 140 shares control of a prosthetic device, such as robotic prosthetic device 190, providing refined motor control and accurate tactile pressure and lift force, based on manipulation data for a particular object that are received from a knowledge base of cognitive system 105 and sensory feedback. In some embodiments, manually initiated control of the prosthetic device remains operational and may interrupt or override mobile control device 140 as deemed appropriate by the user of the prosthesis.

Robotic support device 160 is depicted supporting a human arm that lacks motor function, strength, or control to perform normal activities. In some embodiments of the present invention, robotic support device 160 is a type of prosthetic device that includes motors and components enabling assisted movement of arm supported. In such embodiments, robotic support device 160 is controlled wirelessly by mobile control device 140.

Camera 170 is located in a vicinity of a user of a robotic prosthetic device, such as robotic prosthetic device 190. In some embodiments of the present invention, camera 170 is external to the user and prosthesis, and includes a view of an immediate area of the user, including the user and objects within the field of view. Camera 170 is operative coupled to cognitive system 105, and produces images and transmits the images to cognitive system 105 via network 150, from which cognitive system 105 performs analytics on the image to determine an object within the image. Cognitive system 105 utilizes attributes of the object to search a knowledge base for a match; determining a percentage of confidence of the match between the analyzed object image, and stored attributes of an object within the knowledge base. In some embodiments of the present invention, camera 170 may be one or a set of video cameras from which one or more images may be transmitted to cognitive system 105 for analysis. In some embodiments of the present invention, camera 170 includes a view of the facial expressions and other body and appendage positions of the user, and the user's prosthesis. Camera 170 may provide image data that is used to determine the focus of the user as the user directs their eye focus to an object within the immediate area of camera 170, and camera 170 may provide facial expression feedback, as prosthesis manipulation is performed.

In some embodiments of the present invention, augmented reality (AR) glasses 180 may be worn by the user of robotic prosthetic device 190. AR glasses 180 enables the user to view an object within the immediate vicinity and enables the user to indicate selection of the object to be manipulated by robotic prosthetic device 190. In some embodiments of the present invention, AR glasses 180 may enable interaction with mobile control device 140, such as interruption of manipulation interaction with an object utilizing data from cognitive system 105. In other embodiments, AR glasses 180 allows user input and control of a prosthetic device via mobile control device 140. AR glasses 180 may include AR glasses camera 187, operatively coupled with cognitive system 105, which enables image capture of an object for selection, and may provide images to cognitive system 105 for analytic processing and object identification. AR glasses 180 connects to AR glasses transceiver 185, which provides wireless connection of AR glasses 180 and AR glasses camera 187 to cognitive system 105 and mobile control device 140 via wireless connection 130 and network 150. In other embodiments, images received by AR glasses camera 187 during manually operated manipulation of an object may be included in machine learning processes and included in personalized knowledge base 120 and/or master knowledge base 110.

In some embodiments of the present invention, camera 170 and AR glasses camera 187 are considered "operatively coupled" to cognitive system 105 and can be one or more cameras in close proximity of the user of the prosthetic device and the object of interest to be manipulated. One or more cameras provide a view of the user's facial expressions, focus of the eyes, and body position and movement as feedback of selection and manipulation. In other embodiments, cameras operatively coupled to cognitive system 105 may be connected to the prosthetic device. For example, one camera may be directed to the manipulative end of the device for images of selection and manipulation, and another camera may be directed towards the user, capturing feedback. In yet other embodiment, images of the object and prosthetic device may be obtained by wearable cameras, such as AR glasses 180 that include AR glasses camera 187. AR glasses 180 may also capture images of the user's eye focus to assist in detecting object selection.

Robotic prosthetic device 190 is depicted as a prosthetic arm and hand and is otherwise representative of prosthetic devices for limbs, or portions of limbs. Robotic prosthetic device 190 includes motors and components enabling robotic, assisted movement of one or a combination of: arm, wrist, hand, and finger components of the prosthesis. In some embodiments of the present invention, robotic prosthetic device 190 is operatively coupled to at least one camera (not shown), enabling view of a user of robotic prosthetic device 190. In some embodiments of the present invention at least one camera, operatively coupled to robotic prosthetic device 190, enables viewing and selection of an object by the user, and provides feedback of manipulation activity (as an alternative or in addition to AR glasses camera 187). In other embodiments, robotic prosthetic device 190 enables robotic, assisted movement of prosthetic toes, foot, lower leg and upper leg (not shown). Robotic prosthetic device 190 receives manipulation data from mobile control device 140, which transmits control instructions to manipulate components of the prosthetic device, which may be accessed from personalized knowledge base 120, or master knowledge base 110, for example. Embodiments of the present invention utilize cognitive system 105, and manipulation data of personalized knowledge base 120 and master knowledge base 110 to provide finer control, accuracy, pressure, lift force, and speed to manipulation of a prosthetic device, as compared to manual or discovery-based operation.

Server 101 is depicted as including cognitive system 105, having components of image analytics 125, manipulation program 300, object data program 200, master knowledge base 110, and personalized knowledge base 120. In some embodiments of the present invention, server 101 can be a management server, a web server, a mobile computing device, or any other electronic device or computing system capable of receiving, sending, and processing data, and supporting the operational functions of object data program 200 and manipulation program 300. In other embodiments, server 101 can represent a server computing system utilizing multiple computers as a server system, such as in a cloud computing environment. In still other embodiments, server 101 can be a laptop computer, a tablet computer, a netbook computer, a personal computer (PC), a desktop computer, a personal digital assistant (PDA), a smart phone, or any programmable electronic device capable of performing programmable instructions of object data program 200 and manipulation program 300, and enabling access of data to and from cognitive system 105, mobile control device 140, AR glasses transceiver 185, camera 170, and wireless connection 130, within distributed network processing environment 100, via network 150. In another embodiment, server 101 represents a computing system utilizing clustered computers and components (e.g., database server computers, application server computers, etc.) that act as a single pool of seamless resources when accessed within distributed network processing environment 100. Server 101 may include internal and external hardware components, as depicted and described in further detail with respect to FIG. 4.

Cognitive system 105 searches a knowledge base to match an object of the knowledge base to a selected object that is identified based on the image analytic data received, and associates particular manipulation data for a prosthetic device to manipulate the identified object with finer, more accurate, and faster motor control. Cognitive system 105 also performs machine learning, establishing patterns of interaction, from feedback of manual and robotic manipulation of objects to add new manipulation data to a knowledge base, such as master knowledge base 110, or continuously improve existing manipulation data. Manipulation data from cognitive system 105 provides more accurate targeting, grasp pressure, and lift force, with greater operational speed than manual or alternative control methods. Cognitive system 105 includes image analytics 125, master knowledge base 110, personalized knowledge base 120, object data program 200, and manipulation program 300.

Image analytics 125 includes object recognition technology and techniques to distinguish and identify objects within an image. In some embodiments of the present invention, image analytics 125 is an integrated component of cognitive system 105, whereas in other embodiments, image analytics 125 is functionally connected to cognitive system 105, either directly or via network 150 (not shown). Image analytics 125 receives a digitized image and performs object recognition analysis on the image. The recognition of one or more objects within an image includes a confidence metric, typically a percentage, of a degree of certainty that the image object is the recognized object. The degree of certainty of object recognition is utilized by cognitive system 105 to determine whether an object identified in a knowledge base, such as master knowledge base 110, is a match to the object determined within the image. In some embodiments of the present invention, the confidence level of a match between the object identified in a knowledge base search to the recognized image object is compared to a user-set threshold level of certainty. If the threshold level is met or exceeded, the manipulation data associated with the identified object is transmitted to mobile control device 140 to operate the prosthesis and manipulate the object; doing so with greater speed, accuracy, precision, and efficiency than manual or alternative control.

In some embodiments, cognitive system 105 receives biometric and image feedback indicating a level of success or satisfaction with a particular manipulation activity of an object and applies the feedback along with the particular set of manipulation data as input to performing machine learning of optimized manipulation data for the object.

Master knowledge base 110 is a collection of particular interaction patterns mapped to a particular object. The interaction pattern data includes manipulation data specific to a prosthetic device and object. Master knowledge base 110 includes a set of data regarding an object that is utilized by cognitive system 105 to match object recognition data from image analytics 125. Cognitive system 105 searches master knowledge base 110 to determine a match between an object recognized in a received image and a corresponding set of object data included in master knowledge base 110. In some embodiments of the present invention, master knowledge base 110 is shared by more than one user of a particular type of prosthetic device.

Personalized knowledge base 120 serves as an additional or alternative knowledge base and operates similar to master knowledge base 110; however, personalized knowledge base 120 is not shared by multiple users, is located local to mobile control device 140 and receives refinement of particular manipulation data specific to the prosthetic device and the preferences of the prosthetic device's user. In some embodiments of the present invention, personalized knowledge base 120 may receive manipulation data accessed from mater knowledge base 110, and continues to receive machine learning-based adjustments to the data from repetitive use of the received manipulation data, and from facial expression, eye focus, body movement, biometrics, audio, and local sensor haptic feedback.

Object data program 200 gathers and determines optimized manipulation data for an object that is not identified within a predetermined level of confidence from personalized knowledge base 120 or master knowledge base 110. In some embodiments, object data program 200 is initiated by manipulation program 300 failing to recognize or identify a selected object. Object data program 200 gathers data generated by non-automated robotic or manual manipulation of an object that is not identified by cognitive system 105, or for which personalized knowledge base 120 or master knowledge base 110 does not contain manipulation data for the object.

In some embodiments of the present invention, object data program 200 enables establishing an identity of the object and gathers available sensor data from robotic and/or manual manipulations. The input of manipulation data and sensor, camera, audio, and biometric data are applied to machine learning techniques to determine optimal manipulation data for the object. The input also includes provision of an identification of the object, and in some embodiments, may include classification data input, which enables more effective search results for subsequent object identification. In some embodiments of the present invention, the input of manipulation data, object data, and response feedback data, may include use of a system of classification of objects to augment subsequent identification. The classification system may be based on object recognition data from received images, shape, size, and further include tactile, surface attributes, and weight distribution (having a non-obvious center of gravity), available biometrics, camera image, and audio data. The feedback and response data from manipulation activity reflects the user responses to attempts and repetitions of manipulation of the object, and the outcome of manipulation attempts (such as dropping the object, damaging the object, over or under manipulation, slippage, and difficulty in orientation of the object).

Object data program 200 adds the optimized object manipulation data to personalized knowledge base 120, and in some embodiments, determines if the object manipulation data is to be added to master knowledge base 110, from which the object identification and manipulation data may be shared by other users accessing master knowledge base 110. In some embodiments of the present invention, object data program 200 determines if the newly determined object manipulation data is added to master knowledge base 110, which can be provisioned as a user setting to automatically enable adding the object manipulation data to master knowledge base 110 (or not add), or as a user decision for each object having newly generated manipulation data.

Manipulation program 300 determines whether manipulation data is available for an identified selected object and provides the data to mobile control device 140 to perform manipulation operations of the identified object. Manipulation program 300 determines a selection of an object by determining the eye focus of the prosthesis user, from AR glasses camera 187 of AR glasses 180, or from externally located cameras in the proximity of the object and user, connected to cognitive system 105 via network 150. An image of the selected object is transmitted to cognitive system 105, and image analytics 125 applies object recognition techniques to the received image to identify the object that has been selected. The identity of a recognized object is used to initially search in personalized knowledge base 120 for manipulation data associated with the object for the particular user. Search for manipulation data that is personalized for a particular user is prioritized, as the personalized manipulation data is optimized for the particular prosthesis and user. If manipulation data for the identified object is not found within personalized knowledge base 120, manipulation program 300 performs a search in master knowledge base 110. In response to manipulation program 300 locating manipulation data for the target object in personalized knowledge base 120 or master knowledge base 110, manipulation program 300 retrieves and applies the manipulation data to the prosthetic device, to manipulate the object automatically, with greater accuracy, precision, appropriate tactile force, and speed. As the object is manipulated, any manipulation adjustments made by the user of the prosthetic device are included in data gathered and applied to machine learning for the identified object, which continually optimizes the manipulation data of the object from iterations of received input of object manipulation data. In embodiments of the present invention in which the object selected is not identified, manipulation program 300 initiates object data program 200 (signified by "A" in FIG. 4). Similarly, if an identified object lacks manipulation data in both personalized knowledge base 120 and master knowledge base 110, manipulation program 300 defers to object data program 200 to gather non-automated manipulation data, and include a set of manipulation parameters for the object in personalized knowledge base 120, which are optimized from multiple iterations of object manipulation and, if appropriately enabled in a settings file, object data program 200 forwards the manipulation data to master knowledge base 110.

Figure 2:
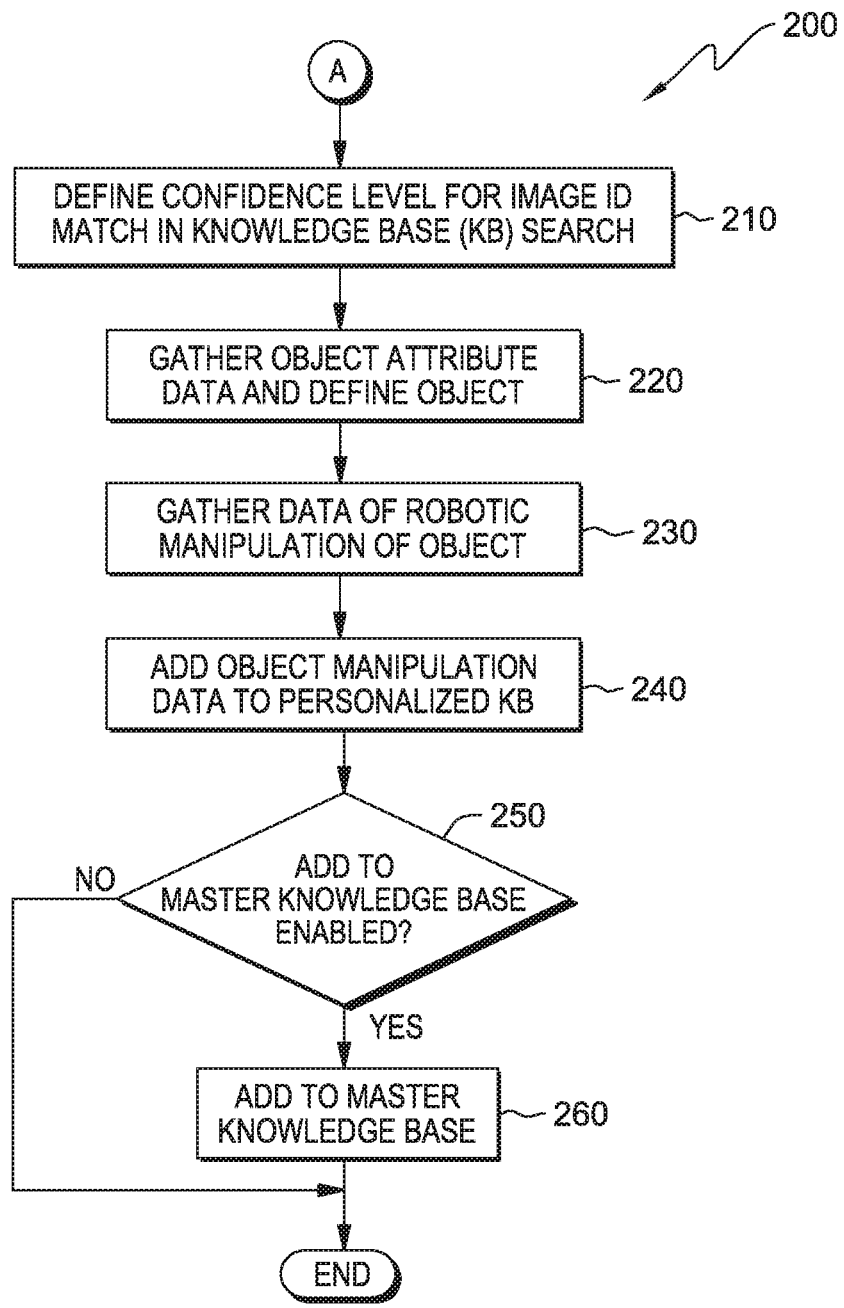
FIG. 2 illustrates operational steps of an object data program, in accordance with an embodiment of the present invention.

FIG. 2 illustrates operational steps of object data program 200, in accordance with an embodiment of the present invention. Object data program 200 initiates in response to manipulation program 300 determining that a selected object is not identified, or if identified, manipulation program 300 determines that no manipulation data exists in either personalized knowledge base 120 or master knowledge base 110. In some embodiments, a query to initiate object data program 200 may be presented to a user as a message or notification, to begin gathering manipulation data of an object known to be absent from object identification databases.

Object data program 200, in step 210, solicits input to define a confidence level at which an object recognized from an image is considered a match when compared to an object identified within a database, or knowledge base of objects, such as master knowledge base 110, or personalized knowledge base 120. In some embodiments, if an object recognized from an image is not identified within master knowledge base 110 or personalized knowledge base 120, object data program 200 may search Internet accessible resources to identify the object and include a confidence level of a match of identification. In some embodiments of the present invention, object data program 200 may present a user with a message request to set the confidence level threshold establishing an acknowledged match. If a confidence level has been previously set, object data program 200 may inquire, by a message on a display device or an audible message, whether the user wishes to edit the current confidence level threshold.

Having indicated to the user that the selected object was not identified, or that manipulation data is unavailable in personalized knowledge base 120 or master knowledge base 110, object data program 200, in step 220, gathers object attribute data and enables identification of the selected object. In some embodiments of the present invention, object data program 200 determines and stores the size, shape, and other physical attributes distinguishable from images of AR glasses camera 187, and/or camera 170, with respect to the selected object. In other embodiments, object data program 200 gathers information input by the user to add identity to the selected object. The object attributes and identity are stored in personalized knowledge base 120. In some embodiments, the prosthetic device contacts the object (for example, as a technique of selecting the object), and sensors included within or on the prosthetic device measure and return data regarding physical attributes of the object, such as the surface roughness, texture, hardness, and uniformity. In some embodiments, object data program 200 determines the weight of the object, and empirically learns the grasping force required to hold and manipulate the object, and/or their limits for holding and manipulating the object selected.

Object data program 200, in step 230, gathers data from the user's robotic manipulation of the object by the prosthetic device, such as robotic prosthetic device 190. The data from the non-automatic manipulation of the prosthetic device is gathered by object data program 200, along with corresponding feedback data, such as facial recognition from camera 170, audio feedback, biometric feedback from sensors connected to the user, and object manipulation results as recorded by AG glasses camera 187. The manipulation data and corresponding feedback data are transmitted to cognitive system 105, and input to machine learning processing to determine more successful and less successful manipulation parameters for the selected object. The non-automatic manipulation includes multiple iterations of manipulating the object, with the accompanying data input to cognitive system 105 via network 150 and processed by machine learning to determine optimized manipulation data for the selected object.

In step 240, object data program 200 adds the object manipulation data, optimized by machine learning, to personalized knowledge base 120. Manipulation program 300 optimizes the manipulation data, as a result of repetitions of non-automated manipulation of the selected object, and transmitting the manipulation image results and corresponding manipulation data to cognitive system 105 for machine learning processing. Object data program 200 adds the optimized manipulation data to personalized knowledge base 120, which provides specific manipulation data that can be used to automatically manipulate the selected object on a subsequent occasion, as will be discussed in detail with respect to FIG. 3. In some embodiments of the present invention, manipulation program 300 may continually optimize the manipulation data corresponding to the selected item, as additional manipulation data and manipulation results feedback are gathered and processed through machine learning of cognitive system 105. The manipulation data corresponding to the selected object includes an identity by which the selected object is recognized and matched to images of the selected object which are subsequently sent to cognitive system 105.

Having added the manipulation data, optimized for the selected object, to personalized knowledge base 120, object data program 200 determines, in decision step 250, whether a feature to add the manipulation data of the selected object to master knowledge base 110 is enabled. For the case in which object data program 200 is determined to not be enabled to add the manipulation data to master knowledge base 110, (step 250, "NO" branch), object data program 200 ends. For the case in which object data program 200 determines that the option to add the manipulation data of the selected object to master knowledge base 110 is enabled (step 250, "YES" branch), object data program 200 transmits the manipulation data of the selected object to master knowledge base 110, in step 260, including transmitting data to identify the selected object by use of object recognition techniques applied to images.

In some embodiments of the present invention, the manipulation data initially added to personalize knowledge base 120, which is subsequently added to master knowledge base 110 is done automatically, and is based on whether an option of object data program 200 to automatically add "new" manipulation data to master knowledge base 110 is enabled. The addition of manipulation data to master knowledge base 110 and personalized knowledge base 120 is based on performing previous searches to match objects recognized in images by image analytics 125 (FIG. 1), and not found in personalized knowledge base 120 or master knowledge base 110. In some embodiments, the option may be included in a settings file of object data program 200. In other embodiments, an option query may be presented to a user as a result of initially adding a particular set of manipulation data of a selected object to personalized knowledge base 120. In yet other embodiments, object data program 200 does not query the user but requires direction from the user to add the particular manipulation data of the selected object to master knowledge base 110.

Having completed adding the manipulation data of the selected object to master knowledge base 110, object data program 200 ends.

Figure 3:
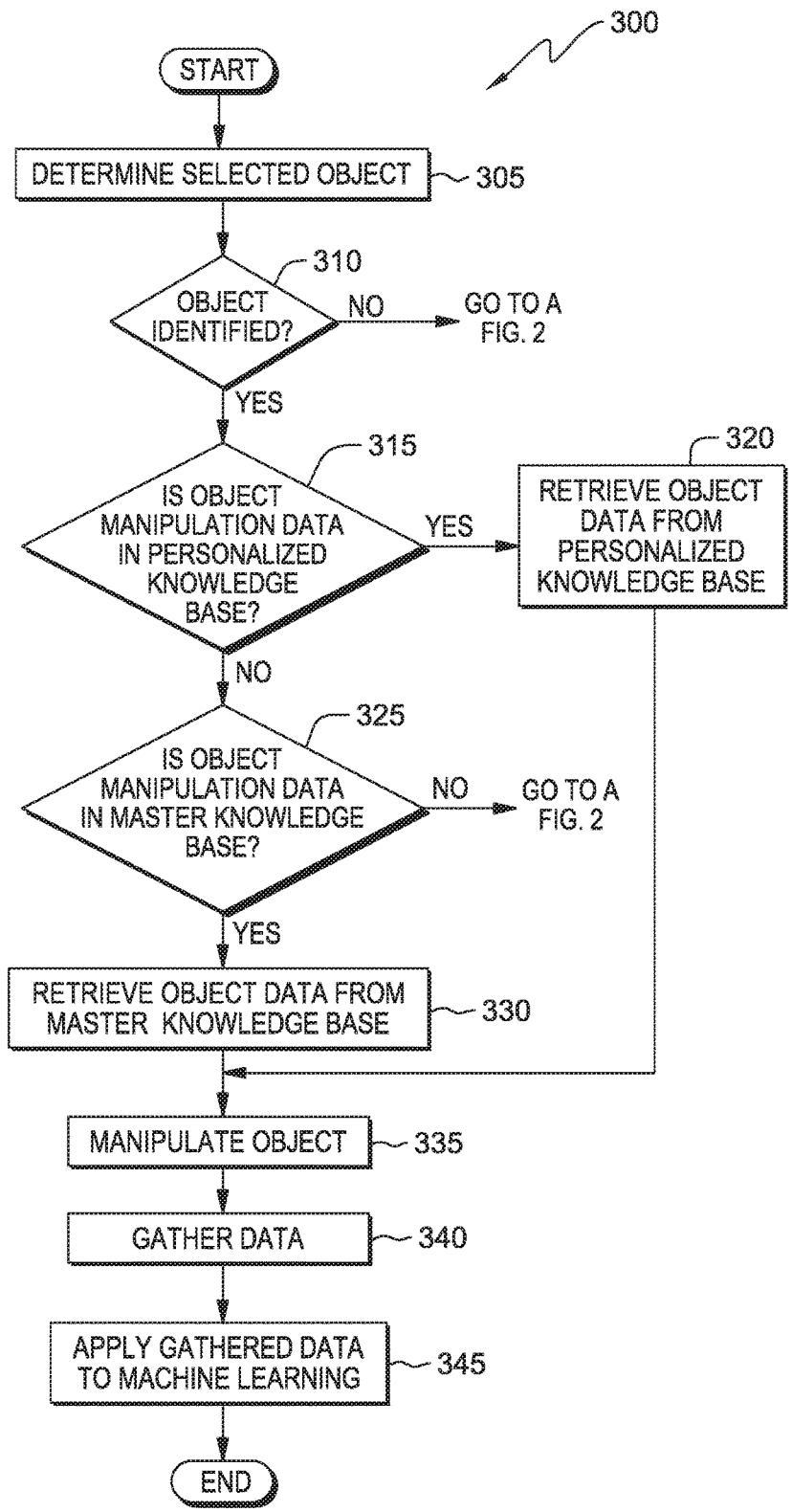
FIG. 3 illustrates operational steps of a manipulation program, in accordance with an embodiment of the present invention.

FIG. 3 illustrates operational steps of manipulation program 300, in accordance with an embodiment of the present invention. Manipulation program 300 determines whether a selected object is identified from images of the selected object compared to object identification data associated with manipulation data, such as data stored in master knowledge base 110 and/or personalized knowledge base 120. If a selected object image is recognized as an identified object within a knowledge base, manipulation program 300 determines if manipulation data exists for the identified object. Available manipulation data is sent to a local controller of the prosthetic device to automatically perform manipulation of the object.

In step 305, manipulation program 300 determines a selected object, which is intended for manipulation. In some embodiments of the present invention, manipulation program 300 utilizes camera images to determine the particular object selected by a user of the prosthetic device. In other embodiments, external cameras are used to determine the selected object by monitoring the eye focus of the user and the viewable area in the immediate vicinity of the user of the prosthetic device. In some embodiments of the present invention, the user may use the prosthetic device to approach or touch the selected object, and in still other embodiments, the selection of the object may be done by verbal command, which is processed using natural language processing techniques. In some embodiments of the present invention, manipulation program 300 confirms the selected object with the user of the prosthetic device.

In decision step 310, manipulation program 300 determines whether the selected object is identified. In some embodiments of the present invention, the identification of the selected object is done by searching a knowledge base, such as personalized knowledge base 120, or master knowledge base 110, or some other repository (not shown in FIG. 1), which contains object data, such as object attribute data determined from image data, and comparing attributes determined from an image of the selected object, to the stored data attributes of objects in the knowledge base or other repository. For example, an image of the selected object may be available from AR glasses camera 187, for a user wearing AR glasses 180. The image of the selected object is sent to cognitive system 105 and is processed using object recognition techniques, performed by image analytics 125, to distinguish and identify objects within the image of the selected object. The identified object of the image is used to perform a search of a knowledge base or other repository of identified object data to determine a confidence level of a match. In some embodiments of the present invention, a similarity function may be used, such as a cosine similarity function, to determine a probability or score regarding whether the identified object of the knowledge base matches the selected object within a predetermined confidence level. The confidence level of a match indicates a relative level of certainty that the object identified from the search matches the object determined from optical recognition of the image of the selected object. The user of the prosthetic device sets a confidence level threshold at or above which the objects are considered to match. For confidence levels below the established threshold, the search result is considered to find no match.

In some embodiments of the present invention, the confidence level is determined by the attributes of one object, such as the image of the selected object, that are found to be common in the other object, such as an identified object from data within a knowledge base of objects. Manipulation program 300 may be configured to indicate the confidence level determined for the object search, and in some embodiments, provide an option for the user to accept a confidence level below the current threshold. For the case in which a search for the object determined from the selected object image indicates no match, or a confidence level below the threshold of a match (step 310, "NO" branch), manipulation program 300 initiates object data program 200 (A), to establish an identity of the selected object and gather manipulation data corresponding to the selected object.

For the case in which an object is identified as a result of searching a knowledge base or repository of object data (step 310, "YES" branch), manipulation program 300 proceeds to decision step 315 to determine if manipulation data for the selected object is found in a personalized knowledge base. In some embodiments of the present invention, the identification of the selected object is used to search personalized knowledge base 120 to determine if manipulation data is found for the selected object. In other embodiments, the search to identify the object may be performed using master knowledge base 110 or another repository of object data or Internet resource. In some embodiments, the initial search to determine whether manipulation data are found for the identified selected object is performed using personalized knowledge base 120. For the case in which manipulation program 300 determines that manipulation data is found in personalized knowledge base 120 (step 315, "YES" branch), manipulation program 300 retrieves the object manipulation data from personalized knowledge base 120, in step 320. In some embodiments of the present invention, retrieval of manipulation data from personalized knowledge base 120 is preferred over manipulation data from master knowledge base 110, because the manipulation data retrieved from personalized knowledge base 120 is specific for the particular user and the user's prosthetic device, such as robotic prosthetic device 190, and may offer additional refinement and precision in manipulating the selected object. Having retrieved the manipulation data for the selected object, manipulation program 300 proceeds to step 335, and performs activity to manipulate the selected object.

For the case in which manipulation program 300 determines that manipulation data is not found in personalized knowledge base 120 for the identified object that is selected, (step 315, "NO" branch), manipulation program 300 proceeds to decision step 325 to determine if manipulation data is found for the identified object that is selected, in a master knowledge base, such as master knowledge base 110. Manipulation program 300 searches master knowledge base 110, based on the determined identification of the selected object, and failing to find manipulation data corresponding to the identified object that is selected (step 325, "NO" branch), manipulation program 300 initiates object data program 200 (A) to establish an identity of the selected object and gather manipulation data corresponding to the selected object, such that the gathering of manipulation data includes gathering feedback data associated with particular manual controlled manipulation activities. Object data program 200 proceeds to gather manipulation data and feedback data, and input the data to cognitive system 105 for machine learning processing to optimize the manipulation data, as described above in regards to FIG. 2.

For the case in which manipulation program 300 determines that manipulation data for the selected object is found in the master knowledge base (step 325, "YES" branch), such as master knowledge base 110, manipulation program 300 proceeds to step 330 and retrieves the object manipulation data from the master knowledge base. In some embodiments of the present invention, the manipulation data for the selected object is retrieved and sent to a local controller of the prosthetic device, such as mobile control device 140. In other embodiments, each manipulation instruction is processed by manipulation program 300 and sent to mobile control device 140 to execute the particular manipulation command.

Having retrieved the manipulation data for the selected object, manipulation program 300 performs manipulation of the selected object, in step 335. Manipulation program 300 receives the manipulation data and sends controller instructions to mobile control device 140, which is local to the prosthetic device, such as robotic prosthetic device 190. Mobile control device 140 receives the manipulation instructions from manipulation program 300 and in turn activates the appropriate motors, switches and other devices enabling robotic prosthetic device 190. The performance of the manipulation data found in master knowledge base 110 enables the manipulation of the selected object with more precision, accuracy, and speed, and includes tactile pressures appropriate for the selected object attributes.

Having manipulated the selected object utilizing the manipulation data found in master knowledge base 110, manipulation program 300 gathers data, in step 340, associated with the manipulation of the selected object. In some embodiments of the present invention, manipulation program 300 monitors the manipulation of the selected object and the feedback data associated with the manipulation activities. In some embodiments of the present invention, the user of the prosthetic device may intervene during automatic processing of manipulation data, and make adjustments or fine tune a particular manipulation activity. The data is gathered by manipulation program 300 capturing the adjustments to automated manipulation data, which can be used or continual refinement and improvement of manipulation of the selected object.

In step 345, manipulation program applies the manipulation data gathered during manipulation of the selected object to machine learning. Manipulation program 300 transmits the manipulation data gathered during manipulation of the selected object to cognitive system 105, to be applied to machine learning in a continuous improvement optimization activity. In some embodiments of the present invention, adjustments made to the automated manipulation data is included in the gathered data, and is input to machine learning which includes changes to the automated manipulation data for the selected object, based on multiple iterations of manipulating the selected object, and considering adjustments made manually by the user of the prosthetic device. In some embodiments, manipulation program 300 may gather manipulation data by initiating object data program 200 to gather the manipulation data and associated feedback data. In other embodiments, manipulation program 300 performs the data gathering activities and transmits the data to cognitive system 105 to be applied to machine learning.

Figure 4:
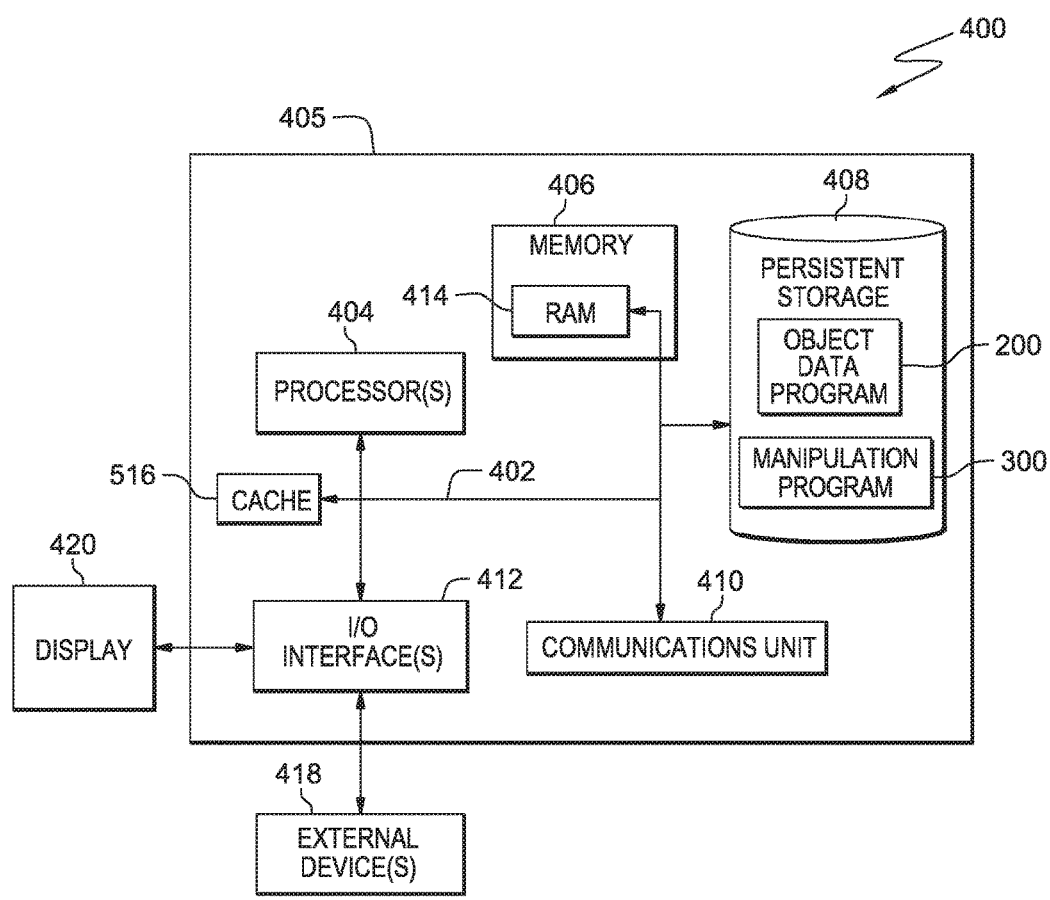
FIG. 4 depicts a block diagram of components of a system, including a computing device capable of operationally performing the object data program and manipulation program, and providing access to object manipulation data, in accordance with an embodiment of the present invention.

FIG. 4 depicts a block diagram of components of a system, including a computing device capable of operationally performing object data program 200 and manipulation program 300, and providing access to object manipulation data, in accordance with an embodiment of the present invention.

Computing device 405 includes components and functional capability similar to server 101, and mobile control device 140 (FIG. 1), in accordance with an illustrative embodiment of the present invention. It should be appreciated that FIG. 4 provides only an illustration of one implementation and does not imply any limitations with regard to the environments in which different embodiments may be implemented. Many modifications to the depicted environment may be made.

Computing device 405 includes communications fabric 402, which provides communications between computer processor(s) 404, memory 406, persistent storage 408, communications unit 410, and input/output (I/O) interface(s) 412. Communications fabric 402 can be implemented with any architecture designed for passing data and/or control information between processors (such as microprocessors, communications and network processors, etc.), system memory, peripheral devices, and any other hardware components within a system. For example, communications fabric 402 can be implemented with one or more buses.

Memory 406, cache memory 416, and persistent storage 408 are computer readable storage media. In this embodiment, memory 406 includes random access memory (RAM) 414. In general, memory 406 can include any suitable volatile or non-volatile computer readable storage media.

Object data program 200 and manipulation program 300 are stored in persistent storage 408 for execution by one or more of the respective computer processors 404 via one or more memories of memory 406. In this embodiment, persistent storage 408 includes a magnetic hard disk drive. Alternatively, or in addition to a magnetic hard disk drive, persistent storage 408 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 408 may also be removable. For example, a removable hard drive may be used for persistent storage 408. Other examples include optical and magnetic disks, thumb drives, and smart cards that are inserted into a drive for transfer onto another computer readable storage medium that is also part of persistent storage 408.

Communications unit 410, in these examples, provides for communications with other data processing systems or devices, including resources of distributed network processing environment 100. In these examples, communications unit 410 includes one or more network interface cards. Communications unit 410 may provide communications through the use of either or both physical and wireless communications links. Object data program 200 and manipulation program 300 may be downloaded to persistent storage 408 through communications unit 410.

I/O interface(s) 412 allows for input and output of data with other devices that may be connected to computing system 400. For example, I/O interface 412 may provide a connection to external devices 418 such as a keyboard, keypad, a touch screen, and/or some other suitable input device. External devices 418 can also include portable computer readable storage media such as, for example, thumb drives, portable optical or magnetic disks, and memory cards. Software and data used to practice embodiments of the present invention, e.g., object data program 200 and manipulation program 300, can be stored on such portable computer readable storage media and can be loaded onto persistent storage 408 via I/O interface(s) 412. I/O interface(s) 412 also connect to a display 420.

Display 420 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method comprising:
one or more processors receiving input that includes image data of an object;
one or more processors determining image attributes of the object, based on performing image analytics on the image data of the object;
one or more processors determining whether the image attributes of the object match image attributes of an identified object of a knowledge base that includes a plurality of identified objects and manipulation data corresponding respectively to the plurality of identified objects,
wherein determining a match between the image data of the object and the identified object of the knowledge base is based on generating a similarity score between the image attributes of the object and the image attributes of the identified object of the knowledge base;
determining whether the similarity score that is generated exceeds a predefined confidence level; and
responsive to determining that the image attributes of the object matches the image attributes of the identified object of the knowledge base, based on the similarity score exceeding the predefined confidence level, one or more processors transmitting manipulation data corresponding to the identified object of the knowledge base, to a mobile controlling device.

2. The method of claim 1, wherein the mobile controlling device is communicatively connected to a manipulation device capable of performing manipulation of the object by utilizing the manipulation data transmitted by the one or more processors, wherein the object for which the input that is received includes the image data of the object, is selected by a user of the manipulation device.

3. The method of claim 1, further comprising:
one or more processors receiving feedback from the manipulation device performing a manipulation of the object, based on the manipulation data of the identified object of the knowledge base, wherein the feedback includes sensory data from the manipulation device and image feedback of the user of the manipulation device during manipulation of the object that is selected by the user;
one or more processors performing machine learning on the feedback of the manipulation of the object selected by the user, based on the manipulation data of the identified object received from the knowledge base, the feedback of the sensory data from the manipulation device, and the image feedback of the user during manipulation of the object that is selected by the user; and
one or more processors adjusting the manipulation data for the object that is selected by the user, based on performing machine learning on the feedback of the sensory data from the manipulation device, and the image feedback of the user during manipulation of the object that is selected by the user.

4. The method of claim 1, further comprising:
one or more processors receiving feedback from the manipulation device performing the manipulation of the object, in which a user of the manipulation device performs adjustments to the manipulation of the object, wherein the feedback is based on the manipulation data corresponding to the identified object received from the knowledge base, and the feedback includes sensory data from sensors operatively connected to the manipulation device, image feedback of the manipulation device from one or more cameras viewing the manipulation device during manipulation of the object, and the adjustments performed by the user;
one or more processors performing machine learning on the manipulation of the object, based on the manipulation data of the identified object received from the knowledge base, the feedback of the sensory data from the sensors connected to the manipulation device, the image feedback received from the one or more cameras viewing the manipulation device during manipulation of the object, and the adjustments performed by the user; and
one or more processors adjusting the manipulation data for the object, resulting from the machine learning applied to the manipulation data of the identified object received from the knowledge base, based on the feedback of the sensory data from the sensors operatively connected to the manipulation device, the image feedback of the manipulation device from the one or more cameras viewing the manipulation device during manipulation of the object, and the adjustments performed by the user.

5. A method comprising:
one or more processors receiving image data of an object selected by a user of a prosthetic device;
one or more processors determining image attributes of the object selected, based on performing image analytics on the image data;
one or more processors determining whether the image attributes of the object selected match an identified object of a knowledge base that includes a plurality of identified objects, wherein an identified object of the plurality of identified objects of the knowledge base includes image attributes and manipulation data corresponding to the identified object; and
responsive to determining that the image attributes of the object selected matches an identified object of the knowledge base, one or more processors transmitting the manipulation data corresponding to the image attributes of the identified object matching the object selected, to a mobile controlling device communicatively connected to the prosthetic device, wherein the mobile controlling device transmits the manipulation data corresponding to the identified object to the prosthetic device.

6. The method of claim 5, further comprising:
one or more processors receiving image data of direction of eye focus, facial expression, and body movement of the user of the prosthetic device from one or more cameras, wherein the image data of the eye focus, the facial expression, and the body movement are directed to an object in view of the user;
one or more processors receiving an image of the object in view of the user of the prosthetic device; and
one or more processors determining the object in view of the user of the prosthetic device is the object selected by the user, based on the image data of the eye focus, the facial expression and the body movement of the user.

7. The method of claim 5, further comprising:
one or more processors receiving feedback from the manipulation device performing a manipulation of the object selected by the user, based on the manipulation data of the identified object of the knowledge base, wherein the feedback includes sensory data from the prosthetic device and image feedback of the user during manipulation of the object selected;
one or more processors performing machine learning on the feedback of the manipulation of the object selected by the user, based on the manipulation data of the identified object received from the knowledge base, the feedback of the sensory data from the prosthetic device, and the image feedback of the user during manipulation of the object selected; and
one or more processors adjusting the manipulation data for the object selected, based on performing machine learning on the manipulation data of the identified object received from the knowledge base, the feedback of the sensory data from the prosthetic device, and the image feedback of the user during manipulation of the object selected by the user.

8. The method of claim 7, wherein the manipulation data that is adjusted for the object selected is added to a second knowledge base having manipulation data particularly adjusted for the user and the prosthetic device of the user.

9. The method of claim 5, wherein one or more processors determining the object selected fails to match an identified object of the knowledge base that includes a plurality of identified objects, one or more processors providing a notification to the user of the prosthetic device, and inputting one or more iterations of non-automatic manipulation data corresponding to the object selected to machine learning processing.

10. The method of claim 5, wherein the image data is received from one or more cameras connected to the prosthetic device and operatively coupled to a cognitive system performing image analytics on the image data received from the one or more cameras.

11. The method of claim 5, wherein determining a match between the object selected by the user of the prosthetic device and the identified object of the knowledge base, includes determining whether a confidence level of the object selected by the user of the prosthetic device and the identified object of the knowledge base exceeds a predetermined threshold.

12. A computer program product comprising:
one or more computer-readable storage media having program instructions embodied therewith, wherein the program instructions are executable by a computer processor, the program instructions comprising:
program instructions to receive image data of an object selected by a user of a prosthetic device;
program instructions to determine image attributes of the object selected, based on performing image analytics on the image data;
program instructions to determine whether the image attributes of the object selected by the user match image attributes of an identified object of a knowledge base that includes a plurality of identified objects, wherein an identified object of the plurality of identified objects of the knowledge base includes image attributes and manipulation data corresponding to the identified object of the plurality of identified objects of the knowledge base,
and wherein program instructions to determine a match between the image data of the object and the identified object of the knowledge base is based on generating a similarity score between the image attributes of the object and the image attributes of the identified object of the knowledge base;
program instructions to determine whether the similarity score that is generated exceeds a predefined confidence level; and
responsive to determining that the image attributes of the object matches the image attributes of the identified object of the knowledge base, based on the similarity score exceeding the predefined confidence level, program instructions to transmit manipulation data corresponding to the identified object matching the image attribute data of the object selected, to a mobile controlling device communicatively connected to the prosthetic device, wherein the mobile controlling device applies the manipulation data corresponding to the identified object to the prosthetic device.

13. The computer program product of claim 12, further comprising:
program instructions to receive image data of direction of eye focus, facial expression, and body movement of a user of a prosthetic device from one or more cameras, wherein the image data of the eye focus, the facial expression, and the body movement are directed to an object in view of the user;
program instructions to receive an image of the object in view of the user; and
program instructions to determine the object in view of the user is the object selected by the use, based on the image data of the eye focus, the facial expression and the body movement of the user.

14. The computer program product of claim 12, further comprising:
program instructions to receive feedback from the prosthetic device performing the manipulation the object that is selected by the user, based on the manipulation data of the identified object of the knowledge base, wherein the feedback includes sensory data from the prosthetic device and image feedback of the user during manipulation of the object that is selected by the user;
program instructions to perform machine learning on the manipulation of the object that is selected by the user, based on the manipulation data of the identified object received from the knowledge base, the feedback of the sensory data from the prosthetic device, and the image feedback of the user during manipulation of the object selected; and
program instructions to adjust the manipulation data for the object that is selected by the user, based on performing machine learning on the manipulation data of the identified object received from the knowledge base, the feedback of the sensory data from the prosthetic device, and the image feedback of the user during manipulation of the object that is selected by the user.

15. The computer program product of claim 14, wherein the manipulation data that is adjusted for the object selected is added to a second knowledge base having manipulation data particularly adjusted for the user and a particular prosthetic device of the user.

16. The computer program product of claim 12, wherein in response to program instructions determining that the object selected fails to match an identified object of the knowledge base that includes a plurality of identified objects, program instructions to provide a notification to the user of the prosthetic device, and to input one or more iterations of non-automatic manipulation data corresponding to the object selected to machine learning processing.

17. The computer program product of claim 12, wherein the image data is received from one or more cameras connected to the prosthetic device and operatively coupled to a cognitive system performing image analytics on the image data received from the one or more cameras.

18. The computer program product of claim 12, wherein program instructions to determine a match between the object selected and the identified object of the knowledge base, includes program instructions to determine whether a confidence level of the object selected and the identified object of the knowledge base exceeds a predetermined threshold.

19. A computer system comprising:
one or more computer processors;
one or more computer-readable storage media;
program instructions stored on the one or more computer-readable storage media for execution by at least one of the one or more processors, the program instructions comprising:
program instructions to receive image data of an object selected by a user of a prosthetic device;
program instructions to determine image attributes of the object selected, based on performing image analytics on the image data;
program instructions to determine whether the image attributes of the object selected by the user match image attributes of an identified object of a knowledge base that includes a plurality of identified objects, wherein an identified object of the plurality of identified objects of the knowledge base includes image attributes and manipulation data corresponding to the identified object of the plurality of identified objects of the knowledge base,
and wherein program instructions to determine a match between the image data of the object and the identified object of the knowledge base is based on generating a similarity score between the image attributes of the object and the image attributes of the identified object of the knowledge base;
program instructions to determine whether the similarity score that is generated exceeds a predefined confidence level; and
responsive to determining that the image attributes of the object matches the image attributes of the identified object of the knowledge base, based on the similarity score exceeding the predefined confidence level, program instructions to transmit manipulation data corresponding to the identified object matching the image attribute data of the object selected, to a mobile controlling device communicatively connected to the prosthetic device, wherein the mobile controlling device applies the manipulation data corresponding to the identified object to the prosthetic device.

20. The computer system of claim 19, further comprising:
program instructions to receive image data of a direction of eye focus, facial expression, and body movement of a user of a prosthetic device from one or more cameras, wherein the image data of the eye focus, the facial expression, and the body movement are directed to an object in view of the user;
program instructions to receive an image of the object in view of the user; and
program instructions to determine the object in view of the user is the object selected, based on the image data of the eye focus, the facial expression and the body movement of the user.

21. The computer system of claim 19, further comprising:
program instructions to receive feedback from the manipulation device performing a manipulation of the object selected by the user, based on the manipulation data of the identified object of the knowledge base, wherein the feedback includes sensory data from the prosthetic device and image feedback from the user during manipulation of the object selected;
program instructions to perform machine learning on the feedback of the manipulation of the object selected by the user, based on the manipulation data of the identified object received from the knowledge base, the feedback of the sensory data from the prosthetic device, and the image feedback of the user during manipulation of the object selected; and
program instructions to adjust the manipulation data for the object selected, based on performing machine learning on the manipulation data of the identified object received from the knowledge base, the feedback of the sensory data from the prosthetic device, and the image feedback of the user during manipulation of the object selected by the user.

22. The computer system of claim 21, wherein the manipulation data that is adjusted for the object selected is added to a second knowledge base having manipulation data particularly adjusted for the user and the prosthetic device of the user.

23. The computer system of claim 19, wherein the image data is received from one or more cameras connected to the prosthetic device and operatively coupled to a cognitive system performing image analytics on the image data received from the one or more cameras.

24. The computer system of claim 19, wherein program instructions to determine a match between the object selected and the identified object of the knowledge base includes program instructions to determine whether a confidence level of the object selected and the identified object of the knowledge base exceeds a predetermined threshold.

* * * * *